(12) United States Patent
Tal et al.

(10) Patent No.: US 11,559,285 B2
(45) Date of Patent: Jan. 24, 2023

(54) REFLECTION ULTRASOUND TOMOGRAPHIC IMAGING USING FULL-WAVEFORM INVERSION

(71) Applicant: Vortex Imaging Ltd., Yavne (IL)

(72) Inventors: Uri Tal, Sunnyvale, CA (US); Tomer Ben David, Yavne (IL)

(73) Assignee: VORTEX IMAGING LTD., Ramat Gan (IL)

( * ) Notice: Subject to any disclaimer, the term of this patent is extended or adjusted under 35 U.S.C. 154(b) by 0 days.

(21) Appl. No.: 17/177,227

(22) Filed: Feb. 17, 2021

(65) Prior Publication Data

US 2022/0257217 A1 Aug. 18, 2022

(51) Int. Cl.
*A61B 8/08* (2006.01)
*A61B 8/00* (2006.01)

(52) U.S. Cl.
CPC .............. *A61B 8/5207* (2013.01); *A61B 8/42* (2013.01); *A61B 8/4444* (2013.01); *A61B 8/4477* (2013.01); *A61B 8/4488* (2013.01); *A61B 8/463* (2013.01); *A61B 8/4405* (2013.01)

(58) Field of Classification Search
CPC ....... A61B 8/5207; A61B 8/42; A61B 8/4444; A61B 8/4477; A61B 8/4488; A61B 8/463; A61B 8/4405; G01S 15/8927
See application file for complete search history.

(56) References Cited

U.S. PATENT DOCUMENTS

| | | | | |
|---|---|---|---|---|
| 2011/0130660 | A1* | 6/2011 | Cloutier | A61B 8/5215 600/438 |
| 2014/0364736 | A1* | 12/2014 | Huang | A61B 8/4477 600/447 |
| 2016/0310107 | A1* | 10/2016 | Mansi | A61B 8/485 |
| 2018/0088220 | A1* | 3/2018 | Flynn | G01S 15/8927 |
| 2019/0328355 | A1* | 10/2019 | Calderon Agudo | A61B 6/032 |
| 2020/0008779 | A1 | 1/2020 | Goeksel et al. | |

FOREIGN PATENT DOCUMENTS

CA    2675617 A1    7/2008
WO    WO-2018109490 A1 *  6/2018

OTHER PUBLICATIONS

Roy, O., Zuberi, M. A. H., Pratt, R. G., & Duric, N. (Apr. 2016). Ultrasound breast imaging using frequency domain reverse time migration. In Medical Imaging 2016: Ultrasonic Imaging and Tomography (vol. 9790, p. 97900B). International Society for Optics and Photonics. (Year: 2016).*

(Continued)

*Primary Examiner* — Christopher Koharski
*Assistant Examiner* — James F McDonald
(74) *Attorney, Agent, or Firm* — Kligler & Associates Patent Attorneys Ltd

(57) ABSTRACT

A medical ultrasound (US) imaging system includes a US probe and a processor. The US probe includes an array of transducers arranged in a reflection geometry, the probe configured to emit US waves and to receive reflected ultrasound waves that are reflected from a body portion of a patient. The processor is configured to generate an image of the body portion of the patient by applying an inverse model to the emitted and reflected US waves.

22 Claims, 5 Drawing Sheets

(56) References Cited

OTHER PUBLICATIONS

Agudo, O. C., Guasch, L., Huthwaite, P., & Warner, M. (Jan. 2018). 3D imaging of the breast using full-waveform inversion. In Proc. Int. Workshop Med. Ultrasound Tomogr. (pp. 99-110). (Year: 2018).*
Guasch, L., Calderón Agudo, O., Tang, M. X., Nachev, P., & Warner, M. (2020). Full-waveform inversion imaging of the human brain. NPJ digital medicine, 3(1), 1-12. (Year: 2020).*
Pratt, "Medical Ultrasound Tomography: Lessons from Exploration Geophysics," Proceedings of the International Workshop on Medical Ultrasound Tomography, pp. 65-76, Nov. 1-3, 2017.
Perez-Liva et al., "Time Domain Reconstruction of Sound Speed and Attenuation in Ultrasound Computed Tomography Using full Wave Inversion," The Journal of the Acoustical Society of America, vol. 141, issue 3, pp. 1595-1604, Mar. 2017.
Kuhn, "Ultrasound Medical Imaging Using 2D Viscoacoustic Full-Waveform Inversion," Master's Thesis, Geophysical Institute, Department of Physics, Karlsruhe Institute of Technology, pp. 1-138, Nov. 12, 2018.
International Application # PCT/IB2022/050383 Search Report dated Apr. 24, 2022.

* cited by examiner

REFLECTION ULTRASOUND TOMOGRAPHIC IMAGING USING FULL-WAVEFORM INVERSION

FIELD OF THE INVENTION

The present invention relates generally to medical imaging, and particularly to quantitative ultrasound (US) imaging.

BACKGROUND OF THE INVENTION

Various methods of medical US imaging were considered in the patent literature and in scientific publications. For example, U.S. Patent Application Publication 2020/0008779 describes a medical ultrasound system comprising an ultrasound transducer for emitting and receiving ultrasound, and a processor. The ultrasound transducer is electrically connected to the processor, and the processor is configured to determine an ultrasound based tomographic image subject to ultrasound waves received by the ultrasound transducer in response to ultrasound waves emitted by the ultrasound transducer and scattered and/or reflected by tissue to be investigated.

As another example, a paper by R. Pratt, titled "Medical ultrasound tomography: lessons from exploration geophysics," Proceedings of the International Workshop on Medical Ultrasound Tomography, Nov. 1-3, 2017, Speyer, Germany, describes potential improvements in medical ultrasound transmission tomography based on full-waveform inversion (FWI).

SUMMARY OF THE INVENTION

An embodiment of the present invention that described hereinafter provides a medical ultrasound (US) imaging system including a US probe and a processor. The US probe includes an array of transducers arranged in a reflection geometry, the probe configured to emit US waves and to receive reflected ultrasound waves that are reflected from a body portion of a patient. The processor is configured to generate an image of the body portion of the patient by applying an inverse model to the emitted and reflected US waves.

In some embodiments, in generating the image using the inverse model, the processor is configured to estimate and indicate in the image one or more of (i) a physiological tissue parameter and (ii) a tissue boundary.

In some embodiments, the physiological tissue parameter includes one of local density, local speed of sound, and local energy attenuation within the body portion.

In an embodiment, the inverse model is full-waveform inversion (FWI). In another embodiment, the inverse model is reverse time migration (RTM).

In some embodiments, the processor is configured to apply the inverse model jointly to US waves emitted and reflected at multiple different locations of the probe relative to the body portion.

In some embodiments, the processor is configured to control the probe to emit and receive the ultrasound waves in a sequence of acquisitions, wherein in each acquisition a respective subset of one or more of the transducers emits the ultrasound waves and one or more others of the transducers receive the reflected ultrasound waves.

In an embodiment, the subsets of the transducers are selected to yield a signal to noise ratio (SNR) value that is above a predefined threshold value.

In another embodiment, the subsets of the transducers selected in the sequence of acquisitions form a two-dimensional multi-static basis.

In yet another embodiment, the subsets of the transducers selected in the sequence of acquisitions form a two-dimensional Hadamard basis.

In some embodiments, the processor is configured to apply low pass filtration to the reflected US waves, to generate an initial image of the body portion of the patient using the low pass filtered reflected US waves, and to use the initial image in subsequent inverse model calculations, so as to generate the image.

In some embodiments, the array of transducers is two-dimensional.

In some embodiments, the processor is located remotely from the probe.

There is additionally provided, in accordance with another embodiment of the present invention, a medical ultrasound (US) imaging method including, using a US probe including an array of transducers arranged in a reflection geometry, emitting US waves and receiving reflected ultrasound waves that are reflected from a body portion of a patient. An image of the body portion of the patient is generated by applying an inverse model to the emitted and reflected US waves.

The present invention will be more fully understood from the following detailed description of the embodiments thereof, taken together with the drawings in which:

DETAILED DESCRIPTION OF EMBODIMENTS

OVERVIEW

Unlike tomographic imaging modalities such as CT and MRI, ultrasound (US) images are typically only indicative by nature. Clinical usefulness of a US imaging session heavily depends on user expertise to apply a US system well enough to acquire meaningful images, and also on the ability of a trained radiologist to interpret the acquired US images.

The root cause of this quality of US images derives from the methods of acquisition and reconstruction of such images, which resemble that of sonar. As a result, unlike protocol-based CT and MRI examinations which are, to a large extent, representative of the actual anatomy being imaged, US images are acquired in an ad-hoc and manual manner and are primarily suggestive. Only in very specific cases does a US image meet the quality of modalities such as CT and MRI, such as with breast US images produced by a US transmission tomographic imaging system. However, although acquiring US waves that carry significant information, transmission geometry is cumbersome and often impractical for imaging larger body portions, such as an abdomen or torso.

Embodiments of the present invention that are described hereinafter provide systems, methods and algorithms for tomographic US imaging of the human body using reflection geometry. Portions of the body that can be imaged in this way include, for example, the abdomen, pelvis and heart. In some of the disclosed embodiments a hand-held US probe is optimized to generate and detect US waves for the disclosed reconstruction algorithms and for use with a protocol-based approach of image acquisition.

In some embodiments, an US reflection tomography imaging system is provided that includes an US probe comprising an array of transducers arranged in a reflection geometry, the probe configured to emit ultrasound waves and to receive reflected ultrasound waves that are reflected from a body portion of a patient. The system further includes a processor, which is configured to generate an image of the body portion of the patient by applying an inverse model to the emitted and reflected ultrasound waves.

In one embodiment, the image comprises at least one physiological tissue parameter, generated by applying full-waveform inversion (FWI) to the emitted and reflected ultrasound waves. In another embodiment, the processor is configured to generate an image of the body portion by applying reverse time migration (RTM) model to the emitted and reflected ultrasound waves.

Figure 2:
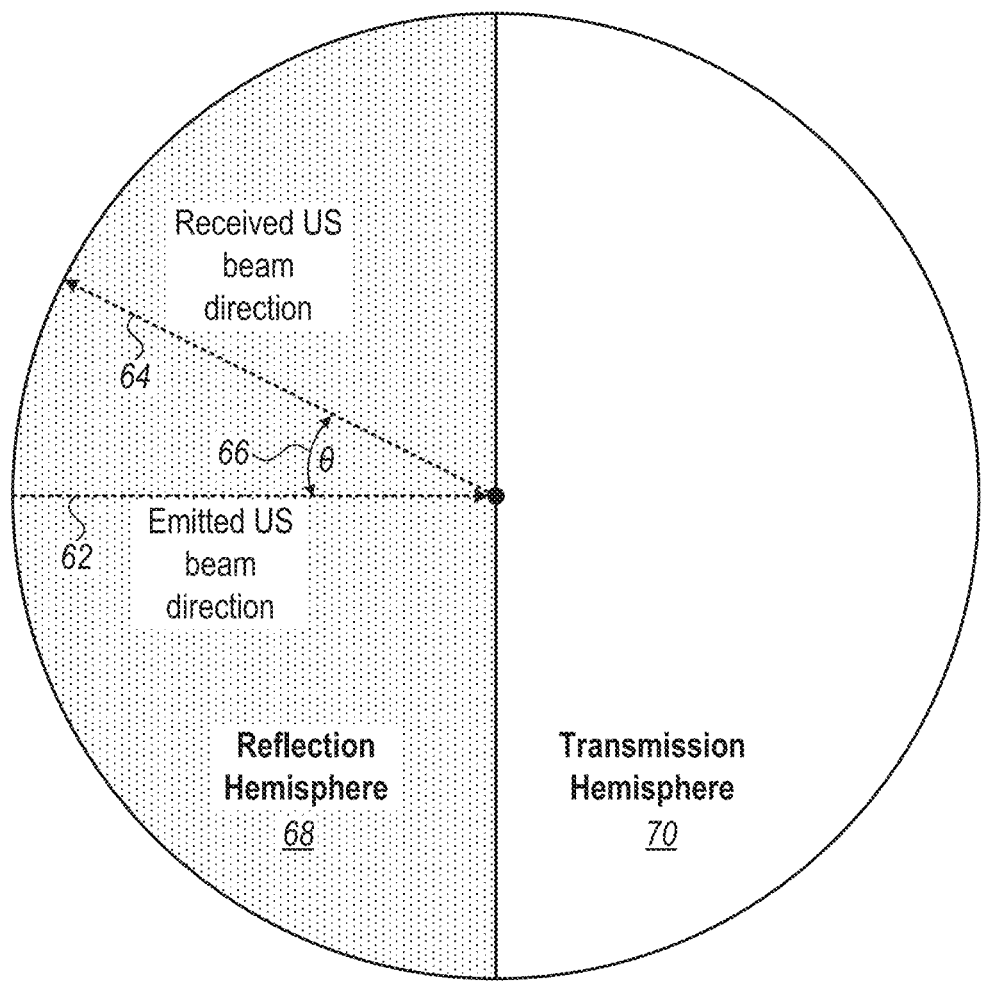
FIG. 2 is a schematic, pictorial illustration of the reflection geometry used by the US reflection tomography imaging system of FIG. 1, in accordance with an embodiment of the present invention.

In the present context, the term "reflection geometry" means a geometry that considers only US waves that, during propagation in the imaged body, change direction relative to the emitted US waves by at least 90 degrees, as shown in FIG. 2 below. Any received beam with such property is considered herein as belonging to a "reflection hemisphere." A two-dimensional transducer-array of a conventional US probe typically captures only a small fraction of such reflection hemisphere (e.g., covers a narrow solid angle, considerably smaller than $2\pi$). Reflection geometry therefore allows the use of probes that capture US waves from a significant portion of the reflection hemisphere. The disclosed reflection tomography imaging systems may use this reflected US waves in order to acquire US data and, using FWI, reconstruct images from the acquired data.

As a rule of thumb for probe design, the depth of imaging using reflection inverse methods is proportional to the aperture of the transducer array of the probe. The proportion coefficient typically varies between 2 to 0.5, and therefore large apertures are required, in a typical range of 5 to 15 cm, depending on the clinical application, on at least one dimension of a two-dimensional array. If the array is longer on one dimension, then the two-dimensional transducer-array is referred to as having a long axis and a short axis (as, for example, in a rectangular array).

The term "inverse model" refers to a class of formal inverse models, such as FWI and RTM, that involve finding medium parameters and/or medium boundaries given a wave equation for an acoustic pressure wave, with some partial measurements of the pressure wave-field at boundaries of the medium, e.g., the emitted and received waves (at the probe) serving as boundary conditions. In general, FWI enables reaching a resolution of half the wavelength of the US signal, which is not achievable with standard methods.

In some disclosed embodiments, the processor applies a FWI algorithm to calculate medium parameters (density, speed of sound, elasticity, etc.) by iteratively applying a procedure of solving the wave equation and comparing the solved wavefield data to actual measurements of wavefield data. In each iteration this comparison yields a small correction to the medium parameters such that eventually the residual error between the solved wavefield and the real measured wavefield is close to zero. At this point, the medium parameters found explain the measured wavefield data well, and in the disclosed embodiments, can be used to generate a quantitative US image, or enhance an image quality of a qualitative US image, such as of a B-mode US image.

In various embodiments of the present invention, the processor uses the reflected US signals to estimate and visualize various physiological tissue parameters to a user. Examples include local tissue density, local speed of sound, local energy attenuation, elasticity and the like.

In one embodiment, the ultrasound probe is configured to generate and detect broadband US waves with an average frequency that is at least an order of magnitude lower than used in conventional modern US systems (e.g., 250 KHz vs. 2.5 MHz or more). Using low pass filters, a low frequency tail of the spectrum of the US signals acquired by the probe (e.g., a tail of frequencies under 100 KHz) is extracted and analyzed. The processor uses the low-frequency tail of the US signal with the FWI algorithm to generate an initial image of the body portion of the patient. Based on the initial image, the processor then uses the higher US frequencies with the FWI algorithm to achieve the full US image with robust and accurate convergence of the FWI algorithm.

In other disclosed embodiments, the processor applies an RTM model to solve the wave equation for the source wavefield Ps (the wavefield is the pressure at every point in space and time, and source means emitted pulses from the source emitters). The RTM model includes taking measured sensor data (from the actual probe) and computationally propagating the received signal backwards in time using the receivers as emitters, this wavefield called Pr. (Mathematically the operation uses the adjoint operator of the wave-equation to run the signal "backwards in time" computationally.) Finally, the processor cross-correlates Ps and Pr (along the time axis) and takes the cross correlation at time−offset=0. This image may not be quantitative, and may result mainly in the sharp edges of the medium (similar properties to b-mode US, but with considerably better accuracy). The RTM method yields especially accurate results if there is a good estimate of the speed of sound in the medium. In this respect, too, the RTM method is similar to b-mode, except that it uses all the data and takes into account complex wave phenomena. The ultrasound b-mode is more like the Kirchhoff migration in geophysics, which is another algorithm that can use be used with the disclosed technique.

In another embodiment, the disclosed probe operates at a frequency range common in conventional modern US systems (e.g., several MHz or higher). Using algorithmic methods, the processor is still capable of achieving the full US image with robust and accurate convergence of the FWI algorithm.

In some embodiments, acquisitions from different locations of the probe, such as from locations over which the probe is moved by a user, are combined. In this way, using the FWI reconstruction algorithm, body depth, spatial resolution and field-of-view (FOV) or the images can be increased.

Unlike conventional US systems that use beamforming techniques to direct an incident US wave (i.e., an US beam that the probe emits) into a particular body location, the disclosed technique emits an US wave that simultaneously covers a large field of view. To this end, in some embodiments the disclosed technique uses the ultrasound probe array in a multi-static acquisition mode. In a simplest form of the multi-static acquisition mode, one transducer emits while the remaining transducers of the array receive reflection signals. In alternative embodiments, the disclosed technique can be used on top of a set of beamformed signals, as long as the probe illuminates the target volume across a sufficient range of different angles and distances.

Alternatively, an equivalent mode of the multi-static acquisition mode can be used, that can yield higher signal to noise ratio (SNR), such as running the acquisition in a Hadamard sequence (i.e., applying US emission in sequence made of Hadamard basis of the emitting transducers). Using an algorithm, the processor can map the Hadamard sequence (or any other suitable sequence) into a simpler multi-static sequence. In an embodiment, the sequence is selected to yield an SNR value that is above a predefined threshold value deemed sufficient for generating clinical images.

By providing US systems and methods capable of generating a quantitative US image in a reflection geometry, high quality and reliable medical images can be achieved with limited resources, having image quality comparable to that achieved by far more cumbersome imaging modalities (e.g., CT and MRI) and related work flows.

SYSTEM DESCRIPTION

Figure 1:
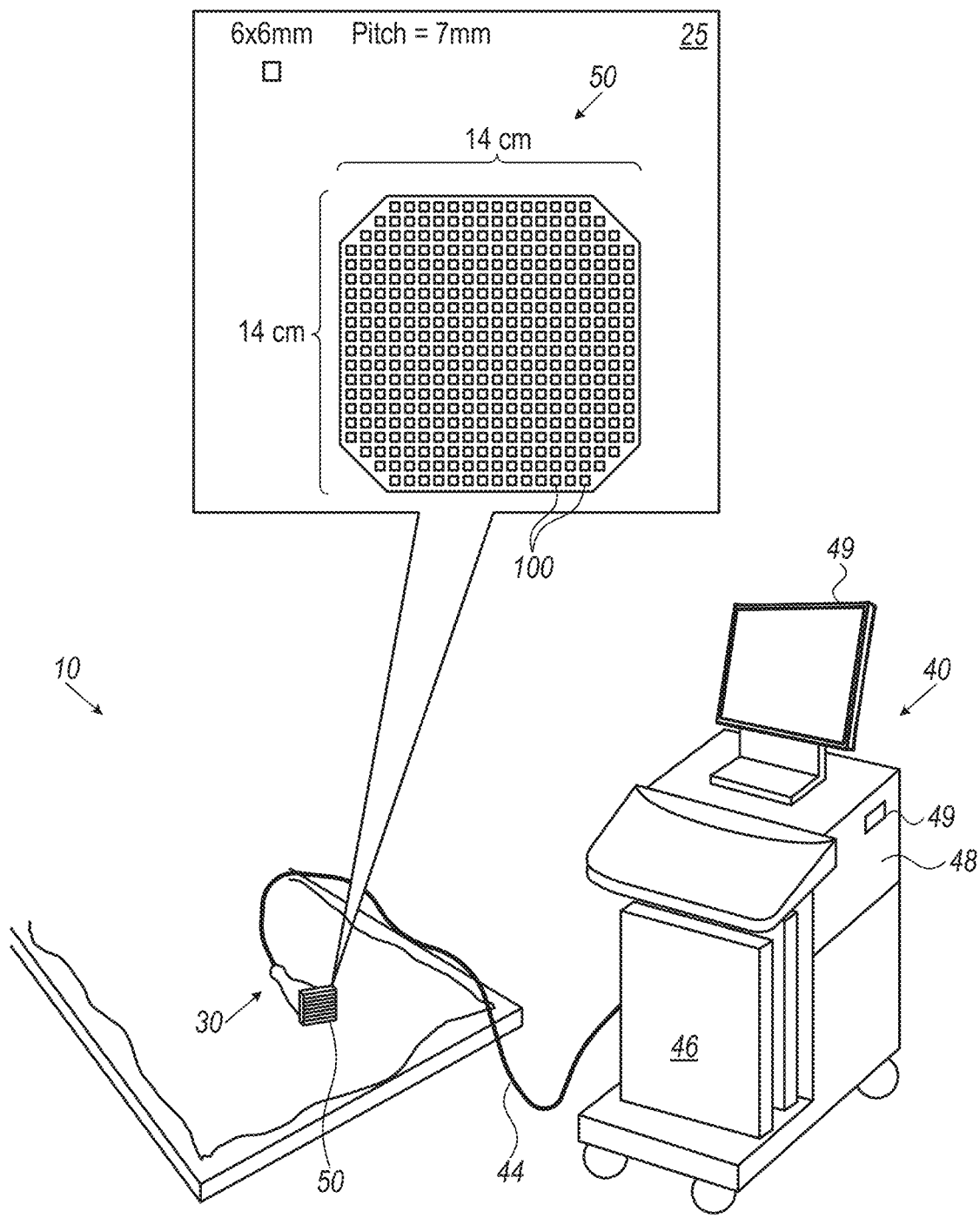
FIG. 1 is a schematic, pictorial illustration of a medical ultrasound (US) reflection tomography system comprising a US probe comprising a flat detector array, in accordance with an embodiment of the present invention.

FIG. 1 is a schematic, pictorial illustration of a medical ultrasound (US) reflection tomography system 10 comprising a hand-held US probe 30 comprising a flat detector array 50, in accordance with an embodiment of the present invention.

US imaging system 10 comprises a US console 40 that comprises an interface 46 to which US probe 30 is connected by a cable 44. Console 40 further comprises a system processor 48.

Interface 46 is configured to pass electrical energy, through cable 44, to array 50 of piezoelectric US transducers 100, which is included in probe 30 and seen in inset 25. US transducers 100 are sized to generate and detect US signals having low-frequency components (e.g., <250 kHz) in order to enable the aforementioned reflection FWI reconstruction of US images. However, other transducer designs may be used, including using transducers sized to generate and detect US signals with a central frequency of 500 KHz or 1 MHz or above, as an example.

High-frequency components of the signals may also be used, for example to increase spatial resolution. Moreover, Interface 46 can be controlled by the processor to pass electrical energy to one or more transducers of the probe in the aforementioned multi-static or other (e.g., Hadamard) acquisition mode that is equivalent to multi-static (the same forming basis), but has a higher SNR.

Array 50 is configured, in response to driving energy, to generate a US beam and to detect the resulting US echoes, and then transmit the resulting electrical signals to processor 48 via cable 44 and interface 46. Processor 48 is configured to generate, by applying FWI reconstruction, a quantitative US image, and to display it on a monitor 49.

In the shown embodiment, array 50 has a square shape with its corners cut and comprises, purely by way of example, 376 transducers 100, each transducer configured to emit and detect US waves with a central frequency of 250 kHz including emitting and detecting significant US energy in frequencies in the 50-100 kHz band. As seen, probe 30 has approximately a same aperture of the array in all lateral directions.

Given the challenge of obtaining a quantitative image using only data from a one-sided probe (a probe having the aforementioned reflection geometry), the disclosed iterative reconstruction starts with the lowest frequencies possible in order to assist, the convergence of the iterative reconstruction.

Typically, processor 48 comprises a general-purpose computer, which is programmed in software to carry out the functions described herein. In some embodiments, processor 48 includes additional processing resources, such as a set of GPUs. Processor 48 is configured to upload, from a memory 49, software that carries out a US image FWI reconstruction algorithm such as the one described in FIG. 2.

The configuration of array 50 is depicted by way of example. Other configurations of array 50 are possible. In the present example, array 50 is planar, i.e., transducers 100 lie in a single plane. Transducers 100 are arranged in a rectangular 11-by-20 layout. In one example, each transducer 100 is 6 mm-by-6 mm in size. The distance between the centers of adjacent transducers (horizontally or vertically) is 7 mm. In another example, each element of the 376 transducers is made of multiple sub-transducers (e.g., 2×2 or 3×3) for example in order to make the production of such elements easier, where the sub-transducers of a given transducer are connected to the same drive using common wiring.

The overall aperture size of the array is thus 14 cm. In alternative embodiments, array 50 may be slightly curved, or made of a flexible material, so as to conform to the body surface. Array 50 may have any other suitable shape, e.g., rectangular, circular or oval, and any suitable number of transducers in any suitable layout.

In an embodiment, the dimensions of individual transducers 100 may vary over array 50, to optimize array 50 detection capabilities, such as to add the capability of emitting and detecting less US power, including at very low frequencies (e.g., <50 kHz), i.e., to increase probe sensitivity, and/or to increase a bandwidth of the emitted US signal to higher frequencies (e.g., >1 MHz).

While FIG. 1 shows one example system layout, embodiments of the disclosed invention may be realized in other ways. For example, in an embodiment, the entire system (e.g., probe, cable, and a processor) are all fitted in one handheld device. In other embodiments, processor 48 is located remotely from the probe, e.g., across a network. The processor may be realized in a cloud computing network or some off-premises computing resource that carries out the reconstruction, and sends reconstructed images to a predefined recipient (e.g., back to display 49 for viewing at the location of the US procedure.).

REFLECTION GEOMETRY FOR US TOMOGRAPHIC IMAGING

FIG. 2 is a schematic, pictorial illustration of the reflection geometry used, at least partially, by US reflection tomography imaging system 10 of FIG. 1, in accordance with an embodiment of the present invention. As noted above, FWI processing based on reflection geometry allows the use of probes that capture a significant portion of a reflection hemisphere 68 that the disclosed reflection tomography imaging systems may apply for acquiring US signals.

FIG. 2 shows, by way of example, one beam that is emitted by a probe in a direction 62 (that can define an x axis). The disclosed embodiments, and in particular the FWI algorithm used, considers only beams received by the probe that belong to a reflection hemisphere. Such beams (e.g., beam 64) form a complementary angle 66, θ, of no more than 90 degrees, meaning the reflected US waves changed direction by at least 90 degrees relative to the direction of incidence. Otherwise, such beam direction falls in a transmission hemisphere 70. Beams falling in transmission hemisphere 70 are typically not considered by the disclosed FWI algorithm.

As noted above, a two-dimensional transducer-array of a conventional US probe typically captures only a fraction of the reflection hemisphere. Thus, the definition in FIG. 2 covers many more possible probe designs for use with the disclosed FWI based US reflection tomography method.

REFLECTION US TOMOGRAPHIC IMAGING USING FWI RECONSTRUCTION

The disclosed section provides an FWI iterative algorithm to reconstruct a tomographic image of a port on of a human body from US reflection data. In order to accurately reconstruct such an image, the body is modeled as a lossy medium in which the acoustic absorption follows a frequency power law of the form of $\alpha(\omega)=\alpha_0\omega^y$, where $\alpha_0 \geq 0$ is an absorption proportionality coefficient, $\alpha_0$ is the temporal frequency, and y is the power law exponent, that, in some cases, can be assumed to be constant and equal to 1.5.

The addition of finite absorption comes on top of the FWI model capabilities to reconstruct an image based only on acoustic contrast properties, such as differences in acoustic impedance of different tissue types, that generate the reflection and scatter signals. In some cases, however, the medium absorption can still be ignored in the model by assuming $\alpha_0=0$.

The disclosed model follows a paper by M. Perez-Liva et al. entitled, "Time domain reconstruction of sound speed and attenuation in ultrasound computed tomography using full wave inversion," published on March 2017 in The Journal of the Acoustical Society of America, 141 (3), p. 1595, which discusses modeling transmission US tomography.

The linear propagation of acoustic waves in this medium can be described by the fractional Laplacian wave equation for an acoustic pressure wave p(r,t) as a function of position r and time t:

$$\left[\frac{1}{c^2}\frac{\partial^2}{\partial t^2} - \nabla^2 - \tau_1(-\nabla^2)^{\frac{y}{2}}\frac{\partial}{\partial t} - \tau_2(-\nabla^2)^{\frac{y+1}{2}}\frac{\partial}{\partial t}\right]p(r,t) = S(r,t) \quad \text{Eq. 1}$$

where S(r,t) is a source term (i.e., US emission from the probe) and C is the speed of sound in the medium, typically 1530 m/sec on average. The final two terms account for acoustic absorption and dispersion, where $\tau_1$ and $\tau_2$ are given by, $$\tau_1 = -2\alpha_0 c^{y-1}, \quad \tau_2 = 2\alpha_0 c^y \tan\left(\frac{\pi y}{2}\right).$$

In the preceding equations, C and $\alpha_0$ may vary as a function of spatial position r.

Figure 3:
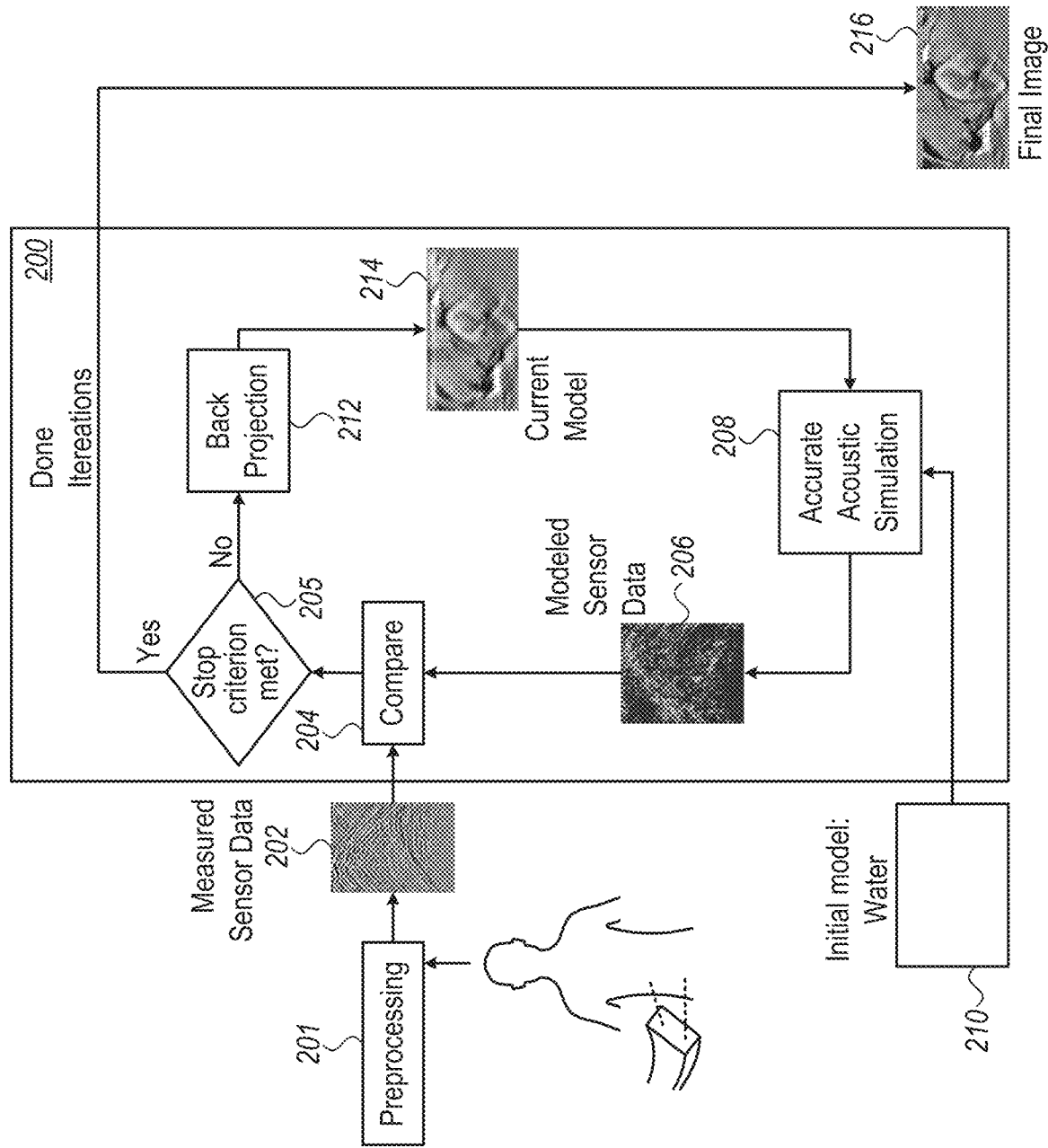
FIG. 3 is a block diagram schematically describing an iterative process of US image FWI reconstruction using data acquired by the system of FIG. 1 and an FWI reconstruction algorithm applied in compliance with the reflection geometry defined in FIG. 2, in accordance with an embodiment of the present invention.

FIG. 3 is a block diagram schematically describing an iterative process of US image FWI reconstruction using data acquired by system 10 of FIG. 1 and an FWI reconstruction algorithm 200 applied in compliance with the reflection geometry defined in FIG. 2, in accordance with an embodiment of the present invention. Typically, processor 48 uploads algorithm 200 from memory 49, and runs algorithm 200 during a US procedure to iteratively solve Eq. 1 to produce a quantitative tomographic image of a portion of the body from US reflection data (including scatter). The quantitative tomographic image may be one or more of local density, local speed of sound, and local energy attenuation images.

As seen in FIG. 3, measured sensor data 202 acquired from reflection into a US probe array, such as array 50, are optionally preprocessed (201) and inputted into an FWI iterative algorithm 200.

A processor running the algorithm compares (204) measured sensor data (202) with a modeled sensor data 206. If a stop criterion is met (at step 205), such as a difference between data being below a given threshold, e.g., as defined by an $L_2$ metric or by a level of misfit in arrival times, or by any other suitable metric, the process stops and a current image 214 becomes the final output image 216. If the stop criterion is not met the iterative calculation continues with a back-projection step 212 of the difference between data, so as to update the modeled medium parameters (e.g., attenuation, speed of sound) and to generate a new image 214, from which acoustic model 208, using Eq. 1, generates a new set of modeled data 206.

As shown in the particular embodiment shown in FIG. 3, at the beginning of the iterative calculations, model 208 is fed with trivial image data (210), such as a uniform value due to a homogenous media (e.g., water).

The example illustration shown in FIG. 3 is chosen purely for the sake of conceptual clarity. FIG. 3 shows only parts relevant to embodiments of the present invention. For example, detailed steps, such as calibrations, are omitted for simplicity.

In some cases, algorithm 200 is run off line, for example by a remote reconstruction and image processing console.

In other embodiments, the disclosed technique is used, in addition to presenting the quantitative images, to generate qualitative images (like the ultrasound b-mode), that are in higher quality and resolution, based on the FWI calculated properties of the medium.

Figure 4A:
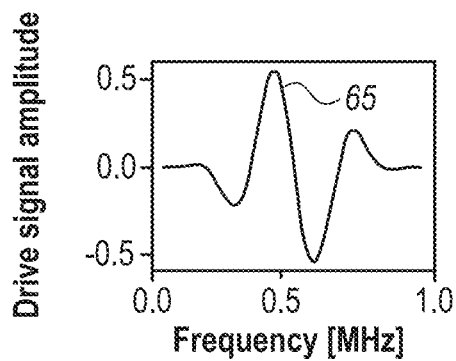
FIGS. 4A and 4B are graphs that show a driving signal spectrum and a simulated spectrum of a resulting US wave emitted by of the system of FIG. 1, respectively, in accordance with an embodiment of the present invention.
Figure 4B:
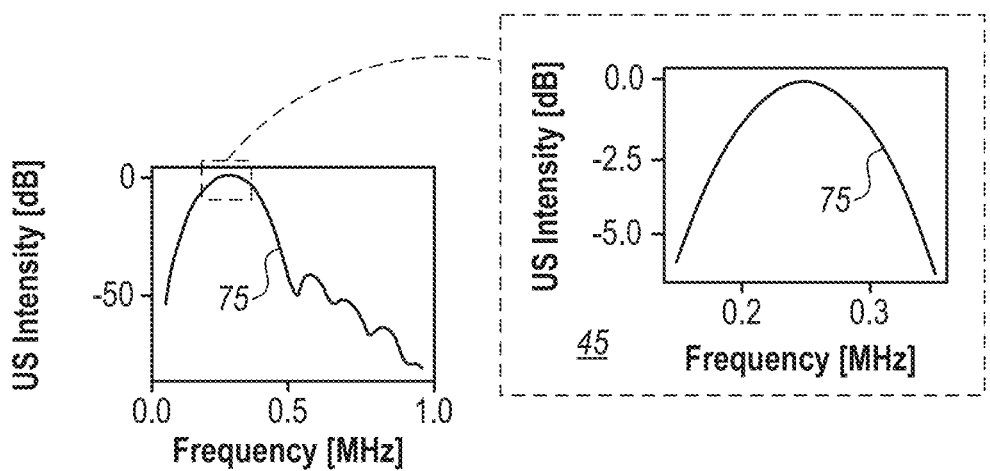

FIGS. 4A and 4B are graphs that show a driving signal spectrum 65 and a simulated spectrum 75 of a resulting US wave emitted by the system of FIG. 1, respectively, in accordance with an embodiment of the present invention.

As seen in FIG. 3A, the driving signal spectrum is made wide (e.g., with a range larger than 0.5 MHz), since the iterative FWI model of FIG. 2 converges better by using data from lower frequencies and increasing data frequency gradually during the reconstruction iterations. Specifically, lower frequencies allow the FWI model to quickly converge close to the global minimum. Higher frequencies increase the spatial resolution of the reconstructed image.

FIG. 3B, and in particular inset 45, show that the peak spectral density of the emitted US wave is at 250 KHz and that substantial portion of the wave energy lies in a tail under 200 KHz and above 300 KHz. Transducers 100 of probe 30 are designed to achieve such US emission and detection profile. In particular the thickness and the composite materials of the transducer elements and the matching layers surrounding them are optimized to this end.

MULTI-STATIC ACQUISITION

Figure 5:
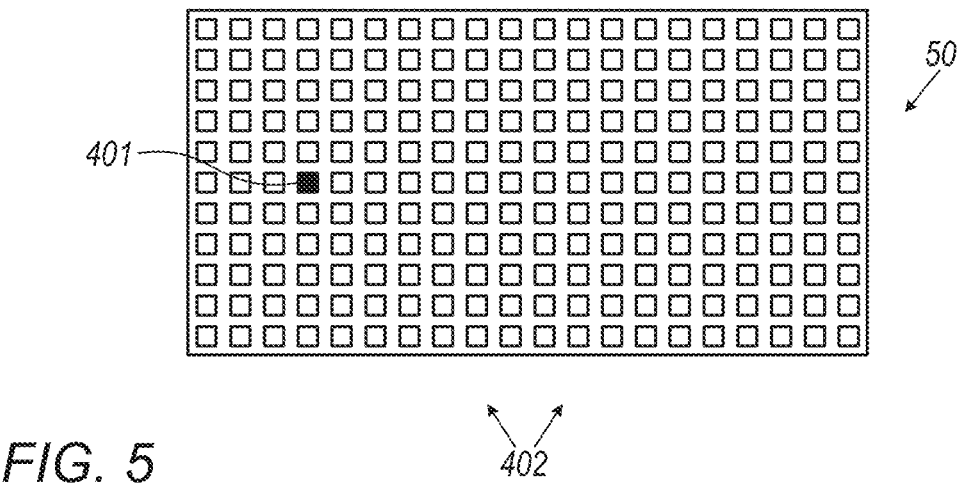
FIG. 5 is a schematic top view of a multi-static acquisition mode used with the US probe of FIG. 1, in accordance with an embodiment of the present invention.

FIG. 5 is a schematic top view of a multi-static acquisition mode used with the US probe of FIG. 1, in accordance with an embodiment of the present invention. In the shown embodiment, at any given acquisition time window, one of the transducers of array 50, e.g., traducer 401 emits, while the rest of the transducers, e.g., traducer 402, receive the resulting signals. The process repeats with each of the transducers of array 50 acting as the transmitter. In the present example, in which array 50 has 376 transducers, a received signal can be arranged as a tensor. The size of the received signal tensor is typically S×R×TS, where S is the number of source emitters, R is the number of receivers, and TS is the number of A/D sampled time-steps. If the emission is done multiple times, N, for example, to increase SNR, per each transducer, then a set of N tensors is obtained. For example, if the number of channels in the acquisition device is limited, a scan can be made repetitive, i.e., making the same emission multiple times (e.g., N), where each time the processor changes the receiving channel multiplexer setting to collect the received signals from all the elements.

In general, there can be acquisition modes that are equivalent to the multi-static acquisition mode described in FIG. 5. For example, in a given acquisition, one or more transducers (e.g., an entire row or column, or any other suitable subset of the transducers) may be used to emit the US waves. At the same time, one or more other transducers (e.g., all remaining transducers) are in a receiving mode. Typically, however, all the transducers are used, as there is no limitation to having the emitting elements become receivers right after they finish emitting their short pulse. Any other sequencing involving using simultaneously more than a single transducer can be considered, such as applying the aforementioned Hadamard basis of transducers.

In some embodiments, transducers of array 50 are excited in a way that allow array 50 to deliver more power into the medium, over a wide range of directions. For example, the array may be excited in a multi-static layout. As another example, the array is excited using a two-dimensional Hadamard basis or using another two-dimensional basis (e.g., Haar), and eventually achieve a multi-static equivalent power delivered with a higher SNR. Nevertheless, as noted above, there is no limitation to using FWI by the disclosed technique on top of a set of beamformed signals, as long as the probe illuminated the target volume across sufficient different angles and distances.

For example, the processor of system 10 can be configured to control probe 30 to operate in a given emission and respective acquisition sequence, where the processor is further configured to, using the given sequence of emitted and reflected US waves transform the acquisition sequence into a multi-static acquisition mode, in which one or more of the transducers are modeled to emitted US waves, and all the transducers are modeled to acquire the reflected US waves (typically, the transducer that transmitted the wave can become a receiver (right after finishing the transmit pulse)). Using the multi-static acquisition mode, the processor generates the image of the body portion of the patient. In particular, the given emission and respective acquisition sequence can be defined by a two-dimensional Hadamard basis.

The disclosed acquisition modes are particularly useful for FWI reconstruction, and can provide extended FOV and depth of imaging.

METHOD OF US IMAGE FWI RECONSTRUCTION IN REFLECTION

Figure 6:
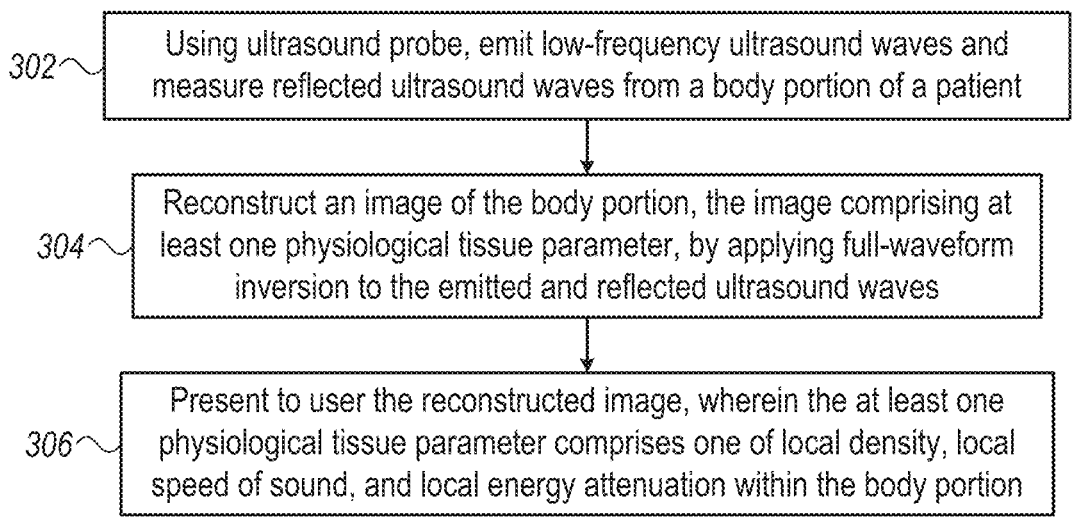
FIG. 6 is a flow chart that schematically illustrates a method for US image FWI reconstruction using data acquired by the system of FIG. 1 and the FWI reconstruction algorithm of FIG. 3, in accordance with an embodiment of the present invention.

FIG. 6 is a flow chart that schematically illustrates a method for US image FWI reconstruction using data acquired by the system, of FIG. 1 and the FWI reconstruction algorithm of FIG. 3, in accordance with an embodiment of the present invention. The process starts with processor 48 receiving reflected ultrasound waves from ultrasound probe 30 that are reflected from a body portion of a patient, at a measured data receiving step 302.

Next, at a US image generation step 304, processor 48 generates an image of the body portion of the patient, the image comprising at least one physiological tissue parameter, by applying full-waveform inversion to the emitted and reflected ultrasound waves. Step 304 may include preprocessing steps such as calibration.

Finally, at an image presenting step 306, the processor presents one or more quantitative US images of at least one physiological tissue parameter. Such images may be of local density, local speed of sound, and local energy attenuation within the body portion.

The example flow chart shown in FIG. 3 is chosen purely for the sake of conceptual clarity. In particular, numerous sub-steps related to the acquisition and reconstruction of the mages are omitted for simplicity of presentation.

Although the embodiments described herein mainly address reflect-on medical ultrasound, the methods and systems described herein can also be used in other applications, such as in nondestructive testing.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical ultrasound (US) imaging system, comprising:
    a US probe comprising an array of transducers arranged in a reflection-only geometry, the probe configured to emit US waves and to receive reflected ultrasound waves that are reflected from a body portion of a patient; and
    a processor, which is configured to generate an image of the body portion of the patient by applying a full-waveform inversion (FWI) process that calculates medium parameters of the body portion by iteratively solving a wave equation and comparing solved wavefield data to actual measurements of the wavefield data, wherein the FWI process is applied only to the US waves emitted from the probe and to the reflected US waves, and not to US waves transmitted through the body portion.

2. The medical ultrasound imaging system according to claim 1, wherein, in generating the image using the FWI process, the processor is configured to estimate and indicate in the image one or more of (i) a physiological tissue parameter and (ii) a tissue boundary.

3. The medical ultrasound imaging system according to claim 2, wherein the physiological tissue parameter comprises one of local density, local speed of sound, and local energy attenuation within the body portion.

4. The medical ultrasound imaging system according to claim 1, wherein the processor is configured to apply the FWI process jointly to the US waves emitted from the probe and to the reflected US waves, at multiple different locations of the probe relative to the body portion.

5. The medical ultrasound imaging system according to claim 1, wherein the processor is configured to control the probe to emit and receive the ultrasound waves in a sequence of acquisitions, wherein in each acquisition a respective subset of one or more of the transducers emits the ultrasound waves and one or more others of the transducers receive the reflected ultrasound waves.

6. The medical ultrasound imaging system according to claim 5, wherein the subsets of the transducers are selected to yield a signal to noise ratio (SNR) value that is above a predefined threshold value.

7. The medical ultrasound imaging system according to claim 5, wherein the subsets of the transducers selected in the sequence of acquisitions form a two-dimensional multistatic basis.

8. The medical ultrasound imaging system according to claim 5, wherein the subsets of the transducers selected in the sequence of acquisitions form a two-dimensional Hadamard basis.

9. The medical ultrasound imaging system according to claim 1, wherein the processor is configured to apply low pass filtration to the reflected US waves, to generate an initial image of the body portion of the patient using the low pass filtered reflected US waves, and to use the initial image in subsequent FWI calculations, so as to generate the image.

10. The medical ultrasound imaging system according to claim 1, wherein the array of transducers is two-dimensional.

11. The medical ultrasound imaging system according to claim 1, wherein the processor is located remotely from the probe.

12. A medical ultrasound (US) imaging method, comprising:
using a US probe comprising an array of transducers arranged in a reflection-only geometry, emitting US waves and receiving reflected ultrasound waves that are reflected from a body portion of a patient; and
generating an image of the body portion of the patient by applying a full-waveform inversion (FWI) process that calculates medium parameters of the body portion by iteratively solving a wave equation and comparing solved wavefield data to actual measurements of the wavefield data, wherein the FWI process is applied only to the US waves emitted from the probe and to the reflected US waves, and not to US waves transmitted through the body portion.

13. The medical ultrasound imaging method according to claim 12, wherein generating the image comprises estimating and indicating in the image one or more of (i) a physiological tissue parameter and (ii) a tissue boundary.

14. The medical ultrasound imaging method according to claim 13, wherein the at least one physiological tissue parameter comprises one of local density, local speed of sound, and local energy attenuation within the body portion.

15. The medical ultrasound imaging method according to claim 12, wherein applying the FWI process comprises applying the FWI process jointly to the US waves emitted from the probe and to the reflected US waves, at multiple different locations of the probe relative to the body portion.

16. The medical ultrasound imaging method according to claim 12, wherein emitting and receiving the ultrasound waves comprises performing a sequence of acquisitions, and in each acquisition emitting the ultrasound waves by a respective subset of one or more of the transducers and receiving the reflected ultrasound waves by one or more others of the transducers.

17. The medical ultrasound imaging method according to claim 16, and comprising selecting the subsets of the transducers to yield a signal to noise ratio (SNR) value that is above a predefined threshold value.

18. The medical ultrasound imaging method according to claim 16, wherein the subsets of the transducers selected in the sequence of acquisitions form a two-dimensional multistatic basis.

19. The medical ultrasound imaging method according to claim 16, wherein the subsets of the transducers selected in the sequence of acquisitions form a two-dimensional Hadamard basis.

20. The medical ultrasound imaging method according to claim 12, wherein applying the FWI process comprises applying low pass filtration to the reflected US waves, generating an initial image of the body portion of the patient using the low pass filtered reflected US waves, and generating the image using the initial image in subsequent FWI calculations.

21. The medical ultrasound imaging method according to claim 12, wherein the array of transducers is two-dimensional.

22. The medical ultrasound imaging method according to claim 13, wherein generating the image is performed remotely from the probe.

* * * * *